United States Patent [19]

Kolloff

[11] Patent Number: 4,735,082

[45] Date of Patent: Apr. 5, 1988

[54] PULSE MODULATED THERMAL CONDUCTIVITY DETECTOR

[75] Inventor: Richard H. Kolloff, West Chester, Pa.

[73] Assignee: Hewlett-Packard Company, Palo Alto, Calif.

[21] Appl. No.: 885,120

[22] Filed: Jul. 14, 1986

[51] Int. Cl.$^4$ ............................................. G01N 25/18
[52] U.S. Cl. ...................................................... 73/27 R
[58] Field of Search ........................................ 73/27 R

[56] References Cited

U.S. PATENT DOCUMENTS

| | | | |
|---|---|---|---|
| 3,913,379 | 10/1975 | Rusz et al. | 73/27 R |
| 4,063,447 | 12/1977 | Mathison | 73/27 R |
| 4,123,934 | 11/1978 | Höht | 73/27 R |
| 4,164,862 | 8/1979 | Jackson | 73/27 R |
| 4,254,654 | 3/1981 | Clouser et al. | 73/27 R |
| 4,461,166 | 7/1984 | Gatten et al. | 73/27 R |

Primary Examiner—Stewart J. Levy
Assistant Examiner—Joseph W. Roskos
Attorney, Agent, or Firm—Donald N. Timbie

[57] ABSTRACT

A thermal conductivity detector comprised of a Wheatstone bridge having a filament in one arm thereof that is contained within a cavity through which the elutant from a column is passed and means for deriving an output signal from one diagonal of the bridge when the voltage applied across the other diagonal is changed from a small value to a large value. In one embodiment, the voltage applied across the one diagonal of the bridge is changed from a fixed low value to a fixed high value and the output signal is the change in the voltage appearing across the other diagonal. In another embodiment, the voltage applied across the one diagonal of the bridge varies from a low value to a value required to keep the bridge in balance, and the difference between these voltages is the output signal.

12 Claims, 2 Drawing Sheets

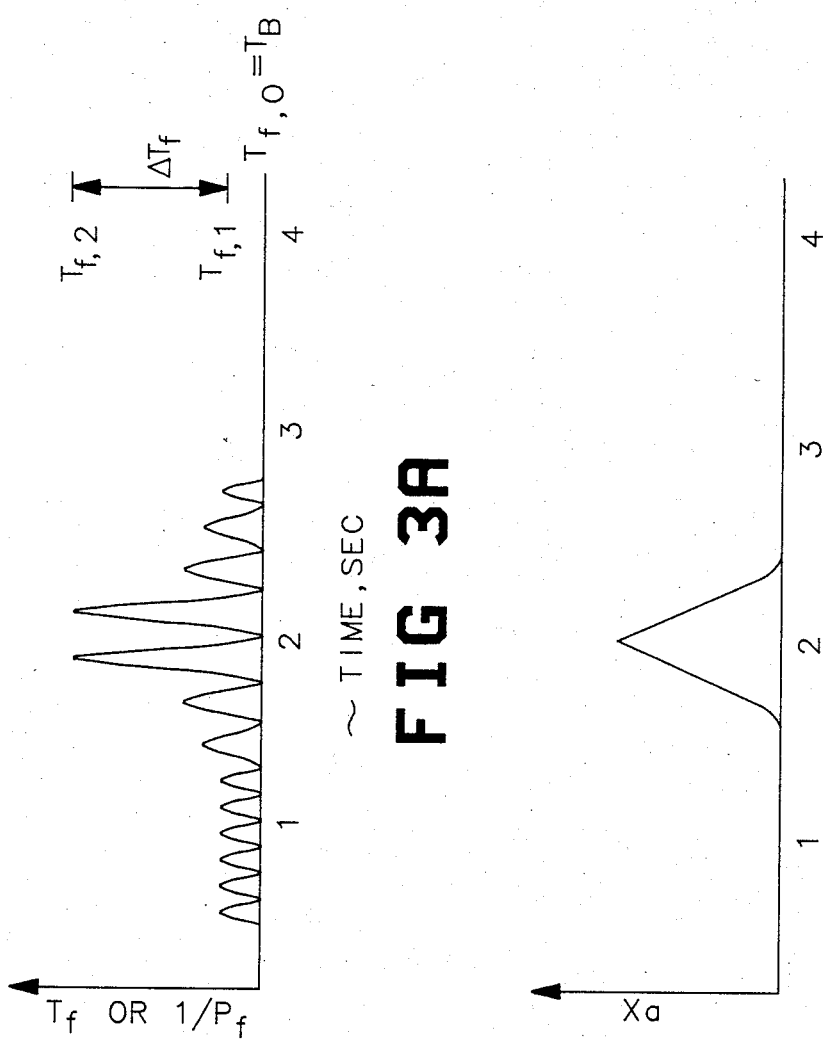

PULSE MODULATED THERMAL CONDUCTIVITY DETECTOR

BACKGROUND OF THE INVENTION

The purpose of chromatography is to determine the respective concentrations of various chemical constituents in matter being examined, e.g., drinking water, suspected toxic waste or blood. In gas chromatography, a sample of the matter having a known volume is injected into a stream of carrier gas as it enters a separation column. The column elutes the constituents in what are referred to as "peaks" at respectively different times from its other end. In each peak, the concentration of the chemical constituent in the carrier gas increases from zero to a maximum and then goes back to zero. The output of the separation column is applied to a detector that produces an electrical output signal corresponding to this peak of changing concentration, and integrating means are provided for deriving a signal corresponding to the area under each peak. The latter signals indicate the relative amounts of the different chemical constituents contained in the injected sample and a comparison with the areas of peaks produced by an injected sample having a known amount of a chemical constitutent indicates the actual amounts of the various constituents contained in the sample being analyzed.

Various types of detectors may be used, but a detector that provides an output signal corresponding to the thermal conductivity of gas contained within it is advantageous because of its universal sensitivity. As it would be difficult to make an accurate measurement of thermal conductivity, the detectors of this type provide a differential output signal related to the relative thermal conductivity of the mixture of constituent and carrier gas in a peak and the carrier gas by itself. For many years, this was done by utilizing a balanced Wheatstone bridge circuit in which two or four arms were essentially identical filaments respectively contained in different cavities within a large metal block and the other two arms were matched resistors. Electrical current was passed through the resistors and the filaments so as to make the temperatures of the filaments greate than that of the metal block. If the gases in the respective cavities had the same thermal conductivity, the rate of heat flow from each filament to the wall of its cavity would be the same so that the resistances of the filaments would still be equal and the bridge would remain in balance; but if the thermal conductivity of the gas in one cavity (which could be carrier gas) were different from the thermal conductivity of gas in the other cavity (which could be constituent gas), the resistances of the filaments would be different and tend to cause an imbalance in the bridge so as to produce an output signal proportional to the imbalance and therefore proportional to the relative thermal conductivities of the gases.

In order to obtain accurate results with such a detector, it is essential that the filaments, cell geometry and wall temperature be identical. The metal block acts as a heat sink having considerable thermal inertia so that the temperature of the walls of the cavities through which the respective gases flow does not change. Before analysis can begin, however, it is essential to operate the detector with carrier gas flowing through both cavities until the bridge becomes stabilized as far as temperature is concerned. Unfortunately, this may require as long as a full day. Drift due to chemical attack on the filaments is always present.

These difficulties were overcome by the thermal conductivity detector described by David E. Clouser and John S. Craven in their U.S. Pat. No. 4,254,654 entitled "Modulated Fluid Detector" which issued on Mar. 10, 1981. It employs a single filament and cell in one arm of a Wheatstone bridge and causes the gas flow through the cell to alternate a number of times during each peak of constituent gas between carrier gas an elutant from the separation column. This produces an output signal that alternates between a value corresponding to the thermal conductivity of carrier gas and a value corresponding to the thermal conductivity of the mixture of carrier and constituent gas. The metal block is not required because the temperature of the wall of the single cell varies so slowly with respect to the rate of alternation as to have substantially the same effect on successive signal values. Synchronous detection techniques are employed to derive an output signal that is the integration of the difference between the signal value attained during one half of the alternation when the constituent gas in the cell and the signal value attained during an adjacent half or the alternation when carrier gas in the cell.

The respective alternate output signal values must obviously be obtained when the cell is full of carrier gas or mixture of constituent and carrier gas. The flow rate required to attain this condition depends on the desired rate of alternation and the cell volume. With the alternation rates of five to ten per second presently desired and with the cells of the smallest practicable volume, the required flow rate is about 5 to 10 sccm/minute, which exceeds that generally used with either narrow or wide bore open tubular columns so that, if the detector is to be used with them, it is necessary to use make-up gas; but no make-up gas is required when the detector is used with packed columns.

BRIEF SUMMARY OF THE DISCLOSURE

The thermal conductivity detector of this invention eliminates the difficulties noted above and, in addition, is useful in analyzing the thermal conductivity of liquids. Different amounts of thermal energy are alternately introduced into the fluid being analyzed, whether gas or liquid, and means are provided for producing a signal indicative of the heat dissipation through the fluid. Integration of the changes in the value of the signal yields a signal indicative of the thermal conductivity of the fluid.

A thermal conductivity detector constructed in accordance with this invention could be comprised of a Wheatston bridge having in one arm thereof a filament contained in a cavity, means for introducing the fluid under analysis into the cavity, means for alternately applying first and second voltages of different values across one diagonal of the bridge and means for deriving an output signal corresponding to the successive differences in voltage appearing across the other diagonal as the first and second voltages are alternately applied. Means are provided for integrating the successive differences so as to provide a signal indicative of the thermal conductivity of gas contained in a peak. No gas switching is required so that no time is lost in waiting for the cavity to fill with carrier gas or a mixture of constituent, henceforth referred to as an analyte, and carrier gas. This means that the cavity can be connected directly to the output of the separation column and that no make-up gas is required, even if the column is a small capillary.

In order to avoid making unnecessary calculations and for attaining maximum sensitivity and accuracy, it is preferable that the temperature and therefore the resistance of the filament be insignificantly changed by the application of the lower of the two voltages. In such case, the temperature of the filament is the same or very nearly the same as the temperature of the walls of the cavity so that no heat flows from the filament to the walls.

In this embodiment of the invention, the filament and the alternate application of voltage across the Wheatstone bridge are the means whereby alternate amounts of thermal energy may be introduced into the cavity, and the bridge and filament are also the means whereby a signal may be derived that is indicative of the amount of thermal energy dissipated through the gas and hece the thermal conductivity of the gas therein.

BRIEF DESCRIPTION OF THE DRAWINGS

FIG. 3A is a graph showing the signal prior to integration; and

FIG. 3B is a graph showing the output signal after integration.

DETAILED DESCRIPTION OF THE INVENTION

Figure 1:
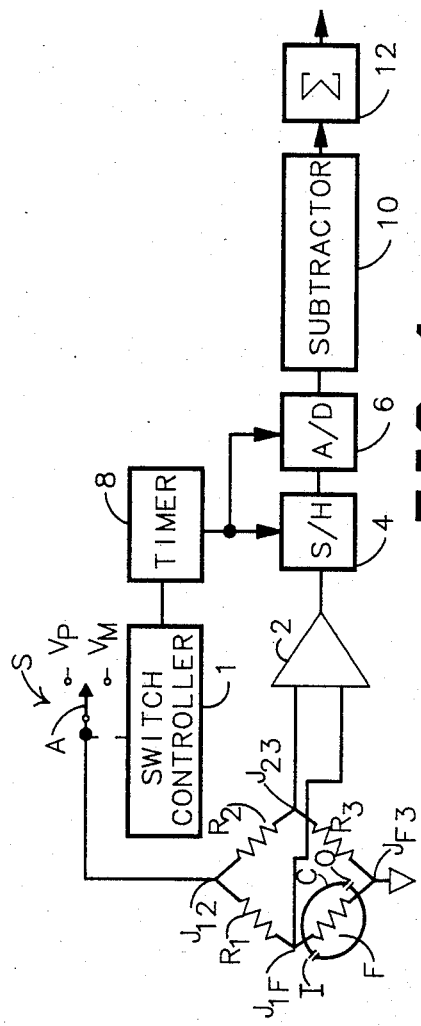
FIG. 1 is a schematic diagram of an embodiment of this invention in which the output signal is the difference in voltage produced across one diagonal when the voltage across the other diagonal is alternated between low and high values.

In FIG. 1, a filament F is shown as being contained in a cavity C having an inlet port I, which can be connected to the output of a separation column, and an outlet port O. The filament F is made of material having a high resistive temperature coefficient so that its resistance changes significantly with temperature, and it is connected as one arm of a Wheatstone bridge having resistors $R_1$, $R_2$ and $R_3$ as its other arms. The resistors $R_1$, $R_2$ and $R_3$ have low temperature coefficients. The junction $J_{F3}$ of the filament F and the resistor $R_3$ is connected to ground, and the junction $J_{12}$ of the resistors $R_1$ and $R_2$ is connected to an arm A of a switch S. The arm A is operated by a switch controller 1 so as to alternately be connected to a high voltage $V_P$ or a lower voltage $V_M$. Preferably, $V_M$ is so low that the current it causes to flow through the filament F does not significantly change its resistance or temperature. The junctions $J_{F3}$ and $J_{12}$ are the ends of one diagonal of the bridge to which operating voltages are applied. The inlet port I is connected to the output of a separation column, not shown.

One input of a differential amplifier 2 is connected to a junction $J_{1F}$ of the resistor $R_1$ and the filament F, and its other input is connected to a junction $J_{23}$ of the resistors $R_2$ and $R_3$. Thus, the inputs of the differential amplifier 2 are connected across the other diagonal of the bridge at which the output voltage of the bridge appears. The output of the amplifier 2 is connected to a sample-and-hold device 4, and its output is connected to an A/D converter 6. A timer 8 causes the switch controller 1 to alternate the arm A between $V_P$ and $V_M$ at such a rate that a number of alternations occur during each peak. The timer 8 also causes the sample-and-hold device 4 and the A/D converter 6 to operate after each change in the position of the switch S. A means 10 provides a signal indicative of the difference between successive samples, and the differences are summed in a summer 12 so as to yield a signal corresponding to the thermal conductivity of a peak in the output of a separation column.

FIG. 1 operates as follows. Whenever the lower voltage $V_M$ is applied across one diagonal $J_{12}$, $J_{F3}$, insufficient current flows through the filament F to change its resistance or temperature by a significant amount. The gases in the cell, the cell walls and the filament F all have the same temperature. Therefore, the voltage across the other diagonal $J_{1F}$, $J_{23}$ will be zero if the resistance of the filament F is the same as the resistances of $R_1$, $R_2$ and $R_3$; but if it is different, the bridge is imbalanced so that the voltage across the said other diagonal will have a value dependent on the temperature involved. Either value, in effect becomes the baseline value. When the higher voltage $V_P$ is applied, the filament F is heated to a higher temperature so as to imbalance the bridge by an amount determ by the resistance attained by the filament F, and this in tur depends on the thermal conductivity of the gases in the cell the time. At each change in the position of the arm A, the sample-and-hold device 4 is operated, and the A/D device 6 stores each sample in digital form. As explained above, the means 10 provides signals respectively corresponding to the difference between the voltage across the diagonal $J_{1F}$, $J_{23}$ for successive samples, i.e., between a sample taken when VM is applied across the diagonal $J_{12}$ and $J_{F3}$, and an adjacent sample taken when $V_p$ is applied across the same diagonal. Thus, variations in the temperatures of the cell walls and the gases do not affect the output of the summer 12 as long as they vary at a rate that is slow compared to the rate at which the arm A is operated. The effect of the temperatures on the thermal conductivity of the gases will have to be taken into account in interpreting the output of the summer 12.

Figure 2:
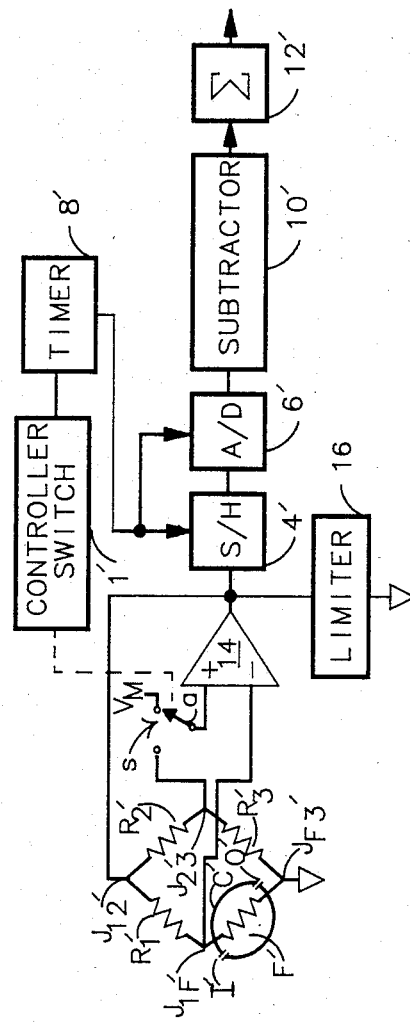
FIG. 2 is a schematic diagram of an embodiment of this invention in which the output signal is that required to bring the bridge into balance.

Reference is now made to the embodiment of the invention shown in FIG. 2 in which components corresponding to those of FIG. 1 are indicated by the same characters primed. A Wheatstone bridge circuit is formed by resistors $R_{1'}$, $R_{2'}$ and $R_{3'}$ and a filament $F'$ that is mounted within a cavity $C'$. The cavity $C'$ has an inlet port $I'$ that is to be connected to the output of a separation column and an outlet port $O'$. The junction $J_{1F'}$ of the filament $F'$ and the resistor $R_{1'}$ is connected to the inverting input of an operational amplifier 14; and the non-inverting input of the operational amplifier is connected to an arm a of a switch s that is operated by a controller $1'$ so as to alternate between a point of voltage $V_M$ and the junction $J_{23'}$ of the resistors $R_{2'}$ and $R_{3'}$. In the latter case, the inputs of the operational amplifier 14 are connected across a diagonal of the bridge at which its output voltage appears. The junction $J_{F3'}$ of the filament $F'$ and the resistor $R_{3'}$ is connected to ground and the junction $J_{12'}$ of the resistors $R_{1'}$ and $R_{2'}$ is connected to the output of the operational amplifier 14 so that the voltage a that output is applied across the other diagonal of the bridge, i.e., $J_{12'}$, $J_{F3'}$. A limiter 16 that is connected between the output of the operational amplifier 14 and ground prevents the output from becoming zero volts or negative. An A/D converter $6'$, a means $10'$ and a summer $12'$ cooperate in the same manner as the corresponding devices 6, 10 and 12 of FIG. 1 to produce a signal indicative of the thermal conductivity of a peak. A time 8' causes the controller 1' to alternate the arm a of the switch s between contact with a source $V_M$ of low voltage and the junction $J_{23'}$ of the resistors $R_{2'}$ and $R_{3'}$, and makes the sample-and-hold device 4' sample the signal at the output of the operational amplifier 14, and the A/D converter 6' sample the output of the sample-and-hold device 4' after each alternation of the switch s.

The operation of the embodiment illustrated by FIG. 2 is as follows. When the arm a of the switch s is connected to the low voltage $V_M$, the output voltage of the amplifier 14 is equal to $R_{1'}/F'$ times $V_M$ and is an indication of the initial imbalance. Since the resistance of the filament F' will change with temperature of the gases in the cell C', this voltage will vary accordingly. When the arm a of the switch s is connected to the junction $J_{23'}$, the initial voltage across the diagonal $J_{12'}$, $J_{F3'}$ is that permitted by the limiter 16, and the inputs of the operational amplifier 14 are connected across the diagonal $J_{F1'}$, $J_{23'}$. In this situation, the amplifier 14 will provide an outp voltage required to heat the filament F' to such temperature that its resistance will bring the bridge into balance. The variation in the voltage at the output of the amplifier 14 during alternate positions of the arm a of the switch s is processed by the S/H device 4', the A/D device 6', the subtractor 10' and the summer 12' to derive the output signal of the detector.

In the embodiment of FIGS. 1 and 2, the output voltage vs. time of the amplifiers 2 and 14 is as indicated in FIG. 3A when the carrier gas has a thermal conductivity greater than that of any constituent gas to be encountered. When a higher voltage is applied across the bridge, the output of either of the amplifiers 2 or 14 increases to a value depending on the concentration of constituent gas in the cavity; and when the lower voltage is applied across the bridge, the output of either of the amplifiers 2 or 14 decreases to a value depending on how close the lower voltage applied across the bridge is to a value that does not increase the temperature of the filament. In FIG. 1, the ordinates of FIG. 3A correspond to the changes in the resistance of the filament F and thus the changes in imbalance in the bridge when different voltages $V_M$ and $V_P$ are applied across it; and in FIG. 2, the ordinates of FIG. 3A correspond to the changes in voltage that must be applied across the bridge in order to keep it in balance.

The waveform in FIG. 3B is the sum of the difference between the amplitudes of successive pulses of FIG. 3A that appear at the output of the subtractors 10 and 10'. When the cavity C contains pure carrier gas, the pulses have constant amplitude so that the output of the subtractors 10 and 10' is zero. Should the temperatures of the wall of the cavities C or C' have a different fixed value during a peak, the tops of the pulses will change in value, but so will the troughs where the voltage $V_M$ is applied.

The calculations set forth below demonstrate that the change in the temperature of the filament resulting from the change in voltage applied to the bridge is related to the thermal conductivity of the analyte or chemical constituent. In these expressions, the subscript "0" indicates a situation where the applied voltage is so small as not to change the temperature of the filament by a significant amount, the subscript "1" indicate a situation where the applied voltage makes a significant change in the temperature of the filament and the cavity containing the filament is filled with carrier gas, and the subscript "2" indicates a situation where the applied voltage makes a significant change in the resistance of the filament and the cavity contains a mixture of carrier gas and constituent or analyte gas. The subscript "f" refers to filament. Various constants used in the equations are defined immediately below. the bridge in order to keep it in balance.

Should the temperatures of the wall of the cavities C or C' have a different fixed value during a peak, the tops of the pulses will change in value, but so will the troughs where the voltage $V_M$ is applied.

The calculations set forth below demonstrate that the change in the temperature of the filament resulting from the change in voltage applied to the bridge is related to the thermal conductivity of the analyte or chemical constituent. In these expressions, the subscript "0" indicates a situation where the applied voltage is so small as not to change the temperature of the filament by a significant amount, the subscript "1" indicate a situation where the applied voltage makes a significant change in the temperature of the filament and the cavity containing the filament is filled with carrier gas, and the subscript "2" indicates a situation where the applied voltage makes a significant change in the resistance of the filament and the cavity contains a mixture of carrier gas and constituent or analyte gas. The subscript "f" refers to filament. Various constants used in the equations are defined immediately below.

$\lambda_c$ = thermal conductivity of carrier gas;
$X_c$ = mole fraction of carrier gas;
$\lambda_a$ = thermal conductivity of analyte;
$X_a$ = mole fraction of analyte;
$G$ = cell geometry factor;
$P$ = power;
$J$ = conversion factor;
$q$ = rate of heat loss from filament;
$m$ = molar flow rate;
$C_p$ = heat capacitance, molar;
$\Delta T'$ and $\Delta T''$ = gas temperature differential between incoming and outgoing streams;
$S'$ and $S''$ = all other heat losses, including radiation and end losses;
$\Delta T$ = difference in temperature of filament and cavity wall;
$\Delta T_f$ = change in filament temperature; and
$\lambda_{c,a}$ = thermal conductivity of mixture of carrier and constituent or analyte gases.
$P_f$ = power dissipated in filament When $\Delta T_0 = 0$, $$\frac{P_{f,0}}{J} = q_0 = G\lambda_c\Delta T_0 = 0, \tag{1}$$

and $$\frac{P_{f,1}}{J} = q_1 = G\lambda_c\Delta T_1 + mC_p\Delta T' + S'. \tag{2}$$

For small changes in $\Delta T_2$ or $\lambda_{c,a}$, $$\frac{P_{f,2}}{J} = q_2 = G\lambda_{c,a}\Delta T_2 + mC_p\Delta T'' + S''; \tag{3}$$

and in the constant power mode, FIG. 1, $$\Delta T_f = (\Delta T_1 - \Delta T_2). \tag{4}$$

Ignoring the second and third terms of equations (2) and (3), solving them for $\Delta T_1$ and $\Delta T_2$ respectively and substituting into equation (4) yields:

$$\Delta T_f = \frac{1}{G}(q_1/\lambda_c - q_2/\lambda_{c,a}) \quad (5)$$

The heat flows $q_1$ and $q_2$ from the filament to the wall of the cavity through carrier gas and carrier gas containing analyte gas respectively are substantially equal for the following reason. For a given temperature difference between the filament and the cavity wall, the heat flow is proportional to the thermal conductivity of the gas in the cavity; but the temperature of the filament varies inversely with the thermal conductivity so as to cause the temperature differential to change in like manner and make a compensating change in the heat flow. The compensation may not be perfect if the differences in the thermal conductivities of the gases is too large because the difference in temperature may affect the thermal conductivities. In most cases, however, this has a small effect. Thus, $$\Delta T_f \approx \left(\frac{P_{f,2}}{JG}\right)\left(\frac{1}{\lambda_c} - \frac{1}{\lambda_{c,a}}\right) \approx \left(\frac{P_{f,1}}{JG}\right)\left(\frac{1}{\lambda_c} - \frac{1}{\lambda_{c,a}}\right) \quad (6)$$

This shows that the change in temperature or resistance of the filament is linearly related to the temperature conductvities of the carrier gas and a mixture of carrier and constituent gases.

Whereas maximum sensitivity would be achieved if the lower voltage $V_M$ applied to the bridge were such as to have no effect on the temperature of the filament, i.e., when $q_0 = 0$, it would be possible to use a lower voltage that would cause the temperature of the filament to increase so that $q_0$ would be other than zero. In this situation, the change in the temperature of the filament would be as follows:

$$\Delta T_f = \frac{1}{G}[(q_1 - q_0)/\lambda_c - (q_2 - q_0)/\lambda_{c,a}] \quad (7)$$

$$= \frac{q_2 - q_0}{G}(1/\lambda_c - 1/\lambda_{c,a})$$

for small changes in $\lambda_{c,a}$ and $\Delta T_f$. By noting the change in the balance of the bridge respectively resulting from the application of different lower voltages, the effect on the output of the summer 12 could be determined.

Although the specific embodiment described has a cavity through which the fluid is passed, there are other ways of alternately introducing different amounts of thermal energy into an analyte and measuring its thermal conductivity. Two probes could be provided: one for alternately introducing different amounts of thermal energy, and the other at a given distance from the first for measuring the amount of thermal energy passed through fluid between them. In another embodiment, a single probe could be used for alternately introducing different amount of thermal energy into the fluid and for measuring the rate at which the thermal energy escaped from the probe.

What is claimed is:

1. A thermal conductivity detector comprising
   means defining a cavity through which fluids to be analyzed may be passed,
   means for alternately introducing different amounts of thermal energy into said cavity, and
   means coupled to said cavity so as to provide signals indicative of the respective difference in the thermal energy transmitted through the fluid therein for successive amounts of energy introduced into said cavity.

2. A thermal conductivity detector, comprising
   a bridge circuit having four resistive arms connected in series, one of said arms including a filament having a temperature responsive resistance,
   means defining a cavity having two ports therein so that fluid to be analyzed may be passed through the cavity,
   means mounting said filament in said cavity,
   means for successively applying voltages of different values across one diagonal of said bridge, and
   means for deriving signals from the other diagonal of said bridge indicative of the imbalance occurring in said bridge during the application of each successive voltage.

3. A thermal conductivity detector as set forth in claim 2 wherein said means for successively applying said different voltages across said one diagonal and for deriving said signals are comprised of
   an operational amplifier having two inputs and an output,
   a circuit for connecting the output of said operational amplifier across said one diagonal,
   a connection between one of said inputs and one end of said other diagonal,
   a source of voltage, and
   a switch for alternately connecting the other input to said source of voltage and to the other end of said diagonal.

4. A thermal conductivity detector as set forth in claim 2 having
   a source of a first voltage,
   a source of a second voltage, and wherein
   said means for alternately applying said different voltages across said one diagonal and for deriving said signals includes a switch for altenately connecting said first and second sources across said one diagonal, and
   said means for deriving signals indicative of the imbalance in said bridge includes an operational amplifier having its inputs respectively connected to opposite ends of said other diagonal.

5. A thermal conductivity detector comprising
   a first resistor and a filament connected in series between two points, said filament and resistor meeting at a junction,
   second and third resistors connected in series between said two points, said second and third resistors meeting at a junction,
   a source of reference potential connected to one of said points,
   an operational amplifier having two inputs and an output, said output of said operational amplifier being connected to the other of said points, and one input of said operational amplifier being connected to one of said junctions,
   a source of voltage,
   a switch for connecting the other of said inputs to the other of said junctions when in one position and to said source of voltage when in the other position, and means coupled to said output of said operational amplifier for deriving the differences between the voltage appearing thereat for successive switch positions.

6. A thermal conductivity detector having means for successively introducing different amounts of thermal energy into a fluid to be analyzed, means for deriving a signal indicative of the thermal energy respectively transmitted through the fluid as successive amounts of energy are introduced thereto, and means coupled to said latter means for deriving an output signal that is a measurement of a parameter of the fluid.

7. A thermal conductivity detector as set forth in claim 6 wherein said means for alternately introducing different amounts of thermal energy into the fluid being analyzed is comprised of a Wheatstone bridge circuit having a filament having a resistance that changes with temperatures in one arm thereof, a cavity, said filament being mounted in said cavity, means for alternately applying different voltages across one diagnonal of said bridge, and said means for deriving said signal being coupled to the other diagonal of said bridge.

8. A thermal conductivity detector as set forth in claim 7 wherein said means for deriving said signal includes an differential amplifier having inputs coupled to said other diagonal so as to produce a voltage corresponding to the change in voltage appearing across said other diagonal when the different voltages are alternately applied across said one diagonal.

9. A thermal conductivity detector as set forth in claim 7 wherein said means for deriving said signal includes an operational amplifier, one input of said operational amplifier being connected to one end of said other diagonal, a source of voltage, and switching means for alternately connecting the other input of said operational amplifier to said source of voltage an to the other end of said other diagonal.

10. A thermal conductivity detector comprising a first resistor and a filament connected in series between two points, said filament and resistor meeting at a junction, second and third resistors connected in series between said two points, said second and third resistors meeting at a junction, a source of reference potential connected to one of said points, an output, an operational amplifier having two inputs and an output, said output of said operational amplifier being connected to the other of said points, and one input of said operational amplifier being connected to one of said junctions, first and second sources of voltage, a switch for alternately connecting said first and second sources of voltage between said points, and means coupled to the output of said operational amplifier for deriving the differences between the voltage appearing at the output of said amplifier for successive switch positions.

11. A thermal conductivity detector comprising means defining a cavity having ports so that fluid to be analyzed can be passed through said cavity, means for successively introducing different amounts of thermal energy to fluid passing through said cavity, means for deriving signals indicative of the thermal energy flowing through said fluid for each amount of energy introduced, and means for deriving from said signals an output signal indicative of a parameter of fluid passing through said cavity.

12. A thermal conductivity detector comprising a temperature responsive resistance, means for successively applying different voltages across said temperature responsive resistance, means coupled to said temperature responsive resistance for deriving signals indicative of the value of its resistance during the application of each of the said voltages, and means for deriving the difference in the voltages produced in response to the application of each successive pair of applied voltages.

* * * * *

UNITED STATES PATENT AND TRADEMARK OFFICE
CERTIFICATE OF CORRECTION

PATENT NO. : 4,735,082
DATED : April 5, 1988
INVENTOR(S) : Richard H. Kolloff

It is certified that error appears in the above-identified patent and that said Letters Patent is hereby corrected as shown below:

Column 1, line 45: change "filaments greate" to -filaments greater--

Column 4, line 23: change "amount determ" to -amount determined-

Column 4, line 24: change "this in tur" to -this in turn-

Column 5, line 2 : change "A time" to -A timer-

Column 4, line 25: change "cell the time" to -cell C at the time--

Column 5, line 22: change "an outp" to -an-output-

Column 8, line 43: change "altenately" to -alternately-

Column 9, line 24: change "diagnonal" to -diagonal-

Column 9, line 29: change "differential amplifier" to -an operational amplifier- Column 10, line 8: change "points, an output" to -points,-

Column 3, line 18: change "and hece" to and -hence-

Signed and Sealed this

Thirteenth Day of March, 1990

Attest:

JEFFREY M. SAMUELS

Attesting Officer      Acting Commissioner of Patents and Trademarks